United States Patent
Kostyniak et al.

(10) Patent No.: US 6,288,076 B1
(45) Date of Patent: *Sep. 11, 2001

(54) ANTIMICROBIAL COMPOSITIONS

(75) Inventors: Paul J. Kostyniak, Amherst; Rossman F. Giese; Patricia M. Costanzo, both of Elma; Joseph A. Syracuse, Tonawanda, all of NY (US)

(73) Assignee: The Research Foundation of State Unversity of New York, Amherst, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/436,407

(22) Filed: Nov. 9, 1999

Related U.S. Application Data

(63) Continuation of application No. 08/807,140, filed on Feb. 27, 1997, now Pat. No. 6,015,816.

(60) Provisional application No. 60/012,513, filed on Feb. 29, 1996.

(51) Int. Cl.$^7$ .................................................. A61K 31/44
(52) U.S. Cl. ............................................................ 514/299
(58) Field of Search ............................... 435/32; 501/146, 501/148; 502/411, 427; 523/508, 521; 514/299

(56) References Cited

U.S. PATENT DOCUMENTS

| | | | |
|---|---|---|---|
| 3,952,105 | 4/1976 | Dorschner | 424/287 |
| 4,054,537 | 10/1977 | Wright et al. | 252/317 |
| 4,081,496 | 3/1978 | Finlayson | 260/864 |
| 4,105,578 | 8/1978 | Finlayson et al. | 252/316 |
| 4,216,135 | 8/1980 | Finlayson | 260/40 R |
| 4,278,047 | 7/1981 | Luca | 119/1 |
| 4,287,086 | 9/1981 | Finlayson et al. | 252/316 |
| 4,306,994 | 12/1981 | Ellslager | 252/382 |
| 4,317,737 | 3/1982 | Oswald et al. | 252/28 |
| 4,365,030 * | 12/1982 | Oswald et al. | 523/508 |
| 4,536,498 | 8/1985 | Tagami et al. | 514/147 |
| 4,929,644 | 5/1990 | Guilbeaux | 514/642 |
| 4,938,955 | 7/1990 | Niira et al. | 424/79 |
| 5,145,674 | 9/1992 | Lane et al. | 424/78.08 |
| 5,169,536 | 12/1992 | Vasconcellos et al. | 210/691 |
| 5,399,343 | 3/1995 | Smith, Jr. | 424/61 |
| 6,015,816 * | 1/2000 | Kostyniak et al. | 514/299 |

FOREIGN PATENT DOCUMENTS

| | | |
|---|---|---|
| 1565362 | 4/1980 | (GB). |
| 63250309 | 10/1988 | (JP). |
| 01316303 | 12/1989 | (JP). |
| 03077801 | 4/1991 | (JP). |
| 4-300801 | 10/1992 | (JP). |
| 07126120 | 5/1995 | (JP). |
| 07173022 | 7/1995 | (JP). |
| 084993 | 3/2000 | (JP). |
| 294597 | 10/2000 | (JP). |
| 318429 | 11/2000 | (JP). |

OTHER PUBLICATIONS

Ohashi et al., "Antimicrobial and Antifungal Agents Derived From Clay Minerals (II): Properties of Montmorillonite Supported by Silver Chelates of 1,10–phenanthroline and 2,2'–dipyridyl," *Applied Clay Science*, 6:301–10 (1992).

Ohashi et al., "Antimicrobial and Antifungal Agents Derived from Clay Minerals," *Journal of Materials Science*, 27:5027–30 (1992).

Ohashi et al., "Antimicrobial and Antifungal Agents Derived From Clay Minerals," *Journal of Materials Science*, 31:3403–07 (1996).

Qawas et al., "The Adsorption of Bactericides by Solids and the Fitting of Adsorption Data to the Langmuir Equation By a Nonlinear Least–Squeare Method," *Pharmaceutic Acta Helvetiae* 61(10–11):314–319 (1986).

Oya et al., Antimicrobial and Antifungal Agents Derived From Clay Minerals (III): Control of Antimicrobial and Antifungal Activities of Ag+–exchanged Montmorillonite by Intercalation of Polyacrylonitrile, *Applied Clay Science*, 6:311–18 (1992).

Yamada et al., "Preparation and Properties of Antibacterial Clay Interlayer Compound," *Kagaku Kogaku Ronbunshu* 17(1):29–34 (1991).

Oya et al., "Antimicrobial and Antifungal Agents Derived from Clay Materials," *Journal of Materials Science* 29(1):11–14 (1994).

Ohashi Antimicrobial and Antifungal Agents Derived from Clay Minerals. J Antibact Antifung Agents 21(11)591–595, 1993.*

* cited by examiner

Primary Examiner—Ralph Gitomer
(74) Attorney, Agent, or Firm—Nixon Peabody LLP

(57) ABSTRACT

The present invention relates to a method of controlling microbial growth on a material or surface. The method includes applying to the material an antimicrobial agent including colloid particles having an ion exchange capacity and having attached a quantity of one or more ligands with antimicrobial properties where the quantity of ligand attached to the colloid particles is in excess of 100% and up to 200% of the ion exchange capacity of the colloid particles. The present invention also relates to a method of controlling mircobial growth in a material. In addition, the present invention relates to an antimicrobial surface, an antimicrobial material, and an antimicrobial agent.

82 Claims, 7 Drawing Sheets

HEPA FILTER WITH NO TREATMENT (3500X)

HEPA FILTER WITH 0.5% SWy/HDTMA TREATMENT (200X)

HEPA FILTER WITH 0.5% LAPONITE/Cu TREATMENT (350X)

HEPA FILTER WITH 0.5% LAPONITE/Cu TREATMENT (1,000X)

ANTIMICROBIAL COMPOSITIONS

This application is a continuation of U.S. patent application Ser. No. 08/807,140, filed Feb. 27, 1997, now U.S. Pat. No. 6,015,816, which claims the benefit of U.S. Provisional Patent Application Ser. No. 60/012,513, filed Feb. 29, 1996.

FIELD OF THE INVENTION

This invention relates generally to an antimicrobial agent and to methods of preventing microbial growth. In particular, the present invention involves an antimicrobial agent containing mineral colloid particles which are modified with antimicrobial ligands.

BACKGROUND OF THE INVENTION

To control microbial growth on a surface, antimicrobials are applied to the surface. Microbial growth in a material can also be controlled by mixing antimicrobials with the material.

One group of compounds commonly used for surface disinfection are quaternary ammonium compounds ("QACs"). The general formula for the QACs is as follows:

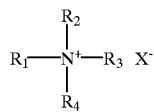

where $R_1$, $R_2$, $R_3$, and $R_4$ are alkyl groups which may be alike or different. Structurally, these compounds contain four carbon atoms linked directly to one nitrogen atom through covalent bonds. The portion attached to the nitrogen by an electrovalent bond may be any anion, but it is usually chloride or bromide to form the salt. The nitrogen atom with the attached alkyl groups forms the positively charged cation portion. Depending on the nature of the R groups, the anion and the number of quaternary nitrogen atoms present, the antimicrobial quaternary ammonium compounds may be classified as monoalkyltrimethyl, monoalkyldimethylbenzyl, heteroaromatic, polysubstituted quaternary, bis-quaternary, or polymeric quaternary ammonium compounds.

Quaternary ammonium compounds have been widely used for disinfection of floors, walls, and equipment surfaces in hospitals, nursing homes, and other public places. Disinfection of these surfaces is carried out by various means, such as an aerosol spray containing quaternary ammonium compounds or a mist of quaternary ammonium compound germicide generated from commercial fogging devices. In addition, QACs have been used in the treatment of food contact surfaces and in outdoor swimming pools and cooling water systems to prevent the proliferation of bacteria. John J. Merianos, "Quaternary Ammonium Antimicrobial Compounds", in *Disinfection, Sterilization and Prevention*, 4th ed. Lea & Fabiger, Philadelphia (1991), which is hereby incorporated by reference.

When QACs are applied directly to surfaces, their effect is not long-lasting due to leaching of the compound from the surface. Therefore, frequent applications may be needed to achieve prolonged antimicrobial effects. As a result, the use of QACs as antimicrobials has not proven to be suitable for surfaces that are not accessible for repeated applications.

The ability to modify the surface of smectite clay minerals by means of a cation exchange with organic cations has been recognized since the 1930s (Gieseking, J. E., "Mechanism of Cation Exchange in the Mont-Morillonite-Beidellite-Nontronite Type of Clay Minerals," *Soil Science*, 47:1–14 (1939), which is hereby incorporated by reference). The quantity of exchangeable cations available on the clay mineral surfaces is given by the cation exchange capacity ("C.E.C."), which has units of milliequivalents (meq)/100 grams of clay. The C.E.C. of smectite clays typically varies between approximately 50 and 150 meq/100 grams. The cation exchange is accomplished by dispersing the clay mineral in water or a mixture of water and a miscible organic solvent such as alcohol in which is dissolved a quantity of the organic cation sufficient to satisfy the C.E.C. of the clay mineral. The organic cation replaces the inorganic cation in a nearly quantitative manner by this single treatment method.

Occasionally, clay minerals are treated with solutions containing an organic cation at greater than the C.E.C. value (as disclosed in U.S. Pat. Nos. 4,116,866, 4,081,496, 4,105, 578, and 4,287,086 to Finlayson; U.S. Pat. Nos. 4,365,030 and 4,317,737 to Oswald, et al.; and U.S. Pat. No. 4,929,644 to Guilbeaux; which are hereby incorporated by reference). However, treatment with an organic cation in excess of the C.E.C. does not ensure that the product will have the exchanged organic material affixed to the clay surfaces in excess of the C.E.C. To definitively establish that the attached organic material exceeds the C.E.C., it is necessary to analyze the quantity of organic material in the organo-clay product. This can be done by determining the carbon content of the product (Ohashi, et al., "Antimicrobial and Antifungal Agents Derived From Clay Minerals: Part IV Properties of Montmorillonite Supported by Silver Chelate of Hypoxanthine," *J. Mat. Sci.*, 27:5027–30 (1992) and Ohashi, et al., "Antimicrobial and Antifungal Agents Derived From Clay Minerals: Part VIII Thermostability of Montmorillonite Intercalated by Silver Chelate of 2-(4-thiazolyl)-benzimidazole or Quaternary Ammonium Salts," *J. Mat. Sci.*, 31:3403–07 (1996), which are hereby incorporated by reference) or by determining the weight loss upon high temperature oxidation of the product.

The typical procedure used to form the organo-clay is to treat the clay mineral by a single exposure to an aqueous solution of the organic cation whose total quantity in the solution is used to determine the C.E.C. equivalents bound to clay mineral (U.S. Pat. No. 4,365,030 to Oswald, et al., which is hereby incorporated by reference).

The utility of organo-clay as antimicrobial compounds has been pointed out by several workers (Oya, et al., "An Antimicrobial and Antifungal Agent Derived From Montmorillonite," *Appl. Clay Sci.*, 6:135–42 (1991); Oya, et al., "Antimicrobial and Antifungal Agents Derived From Clay Minerals (III): Control of Antimicrobial and Antifungal Activities of Ag+-exchanged Montmorillonite by Intercalation of Polyacrylonitrile," *Appl. Clay Sci.*, 6:311–18 (1992); Ohashi, et al., "Antimicrobial and Antifungal Agents Derived From Clay Minerals (II): Properties of Montmorillonite Supported by Silver Chelates of 1,10-phenanthroline and 2,2'-dipyridyl," *Appl. Clay Sci.*, 6:301–10 (1992); and Ohashi, et al., "Antimicrobial and Antifungal Agents Derived From Clay Minerals: Part VIII Thermostability of Montmorillonite Intercalated by Silver Chelate of 2-(4-thiazolyl)-bebzunudazole or Quaternary Ammonium Salts," *J. Mat. Sci.*, 31:3403–07 (1996), which are hereby incorporated by reference). These materials were fabricated by treating the smectite clay mineral with an organic cation or a metal (silver) chelated with an organic cation, all at a quantity sufficient to satisfy the C.E.C. of the clay mineral.

However, none of these references disclose a clay mineral having an organic cation present in excess of the C.E.C. of the clay. Accordingly, the clay materials of the prior art are not entirely satisfactory as compounds having antimicrobial activity.

The present invention is directed to overcoming these above-noted deficiencies by disclosing a process which attaches an antimicrobial ligand to the clay in excess of the C.E.C., thereby imparting increased antimicrobial activity.

SUMMARY OF THE INVENTION

The present invention relates to a method of controlling microbial growth on a material which includes applying to the material an antimicrobial agent. The antimicrobial agent includes mineral colloid particles having an ion exchange capacity and one or more ligands having antimicrobial properties.

Another aspect of the present invention relates to a method of controlling microbial growth in a material. The method includes mixing with the material colloid particles having an ion exchange capacity and having one or more ligands having antimicrobial properties, where the quantity of the ligands attached to the colloid particles is in excess of and up to 200% of the ion exchange capacity of the colloid particles.

Yet another aspect of the present invention relates to an antimicrobial surface coated with colloid particles having one or more ligands with antimicrobial properties.

Yet another aspect of the present invention relates to a material to which antimicrobial properties have been imparted, where the material contains colloid particles having an ion exchange capacity and having ligands with antimicrobial properties, and where the quantity of the ligands attached to the colloidal particles is in excess of and up to 200% of the ion exchange capacity of the colloid particles.

Yet another aspect of the present invention relates to an antimicrobial agent which includes colloid particles having an ion exchange capacity and having one or more ligands with antimicrobial properties, where the quantity of the ligands attached to the colloidal particles is in excess of and up to 200% of the ion exchange capacity of the colloid particles.

Yet another aspect of the present invention relates to a complex having colloid particles having an ion exchange capacity and having one or more ligands, where the quantity of the ligands attached to the colloidal particles is in excess of and up to 200% of the ion exchange capacity of the colloid particles.

The methods, surface, material, antimicrobial agents and colloid particles of the present invention offer advantages not obtainable with the prior art antimicrobials. Because the ligands having antimicrobial properties are strongly bound to the colloid particles of the present invention, the ability of the ligand to leach out is limited. Thus, the antimicrobial agent retains its antimicrobial properties, and the need for repeated coatings to a surface is eliminated or reduced. In addition, because the colloid particles containing a ligand having antimicrobial property are inert, they are less toxic, resulting in ease of handling, use, and disposal. As a coating for a surface, the antimicrobial agent of the present invention is particularly desirable, because it is less costly to coat a surface of a material than to mix the antimicrobial agent throughout the material. The use of the antimicrobial agent as an additive in a material, however, offers other advantages. For example, the antimicrobial agent of the present invention is useful as an inexpensive filler material. Further, when the antimicrobial agent is mixed throughout the material, as the surface of the material wears, fresh antimicrobial is exposed at the surface. In addition, the antimicrobial agent of the present invention includes ligands attached to the colloidal particles in excess of and up to 200% of the C.E.C. of the colloid particles, resulting in greater efficacy of the antimicrobial agent.

DETAILED DESCRIPTION OF THE INVENTION

Figure 1A:
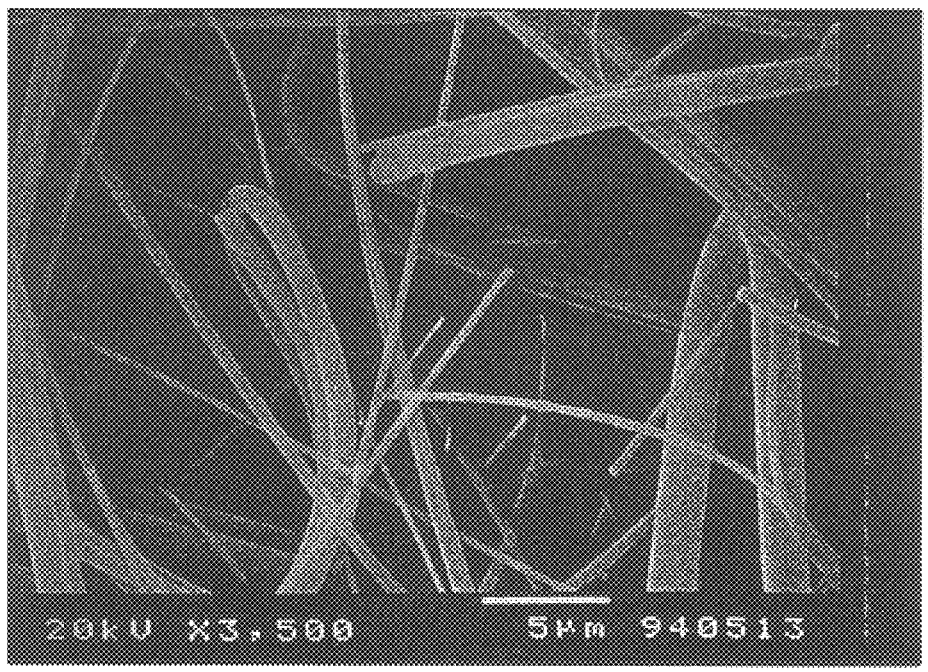
FIG. 1A is a scanning electron microscopy photograph of an untreated HEPA filter.
Figure 1B:
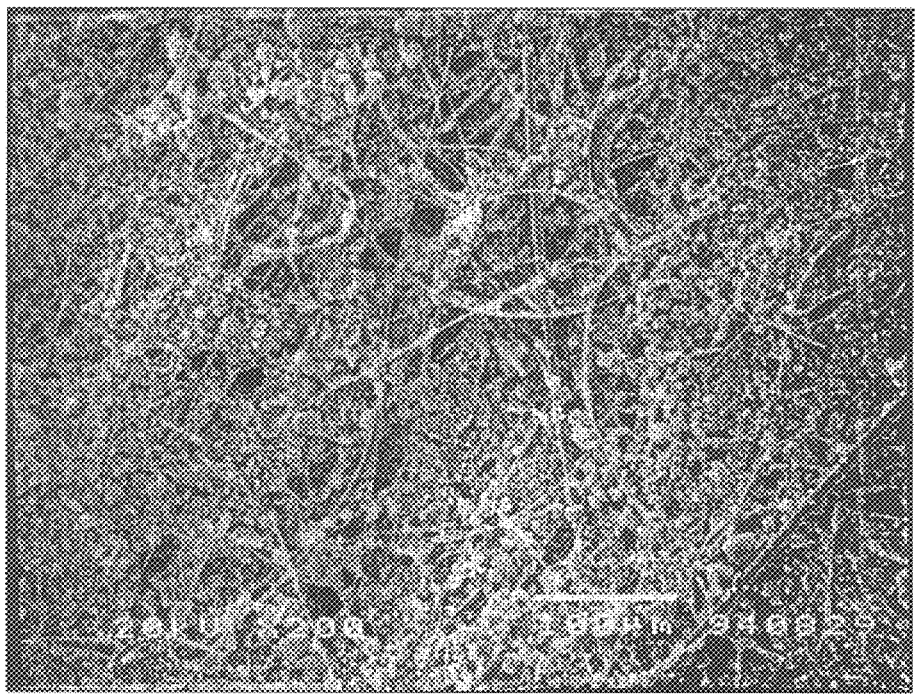
FIG. 1B is a scanning electron microscopy photograph of a HEPA filter treated with the antimicrobial agent of the present invention.
Figure 2A:
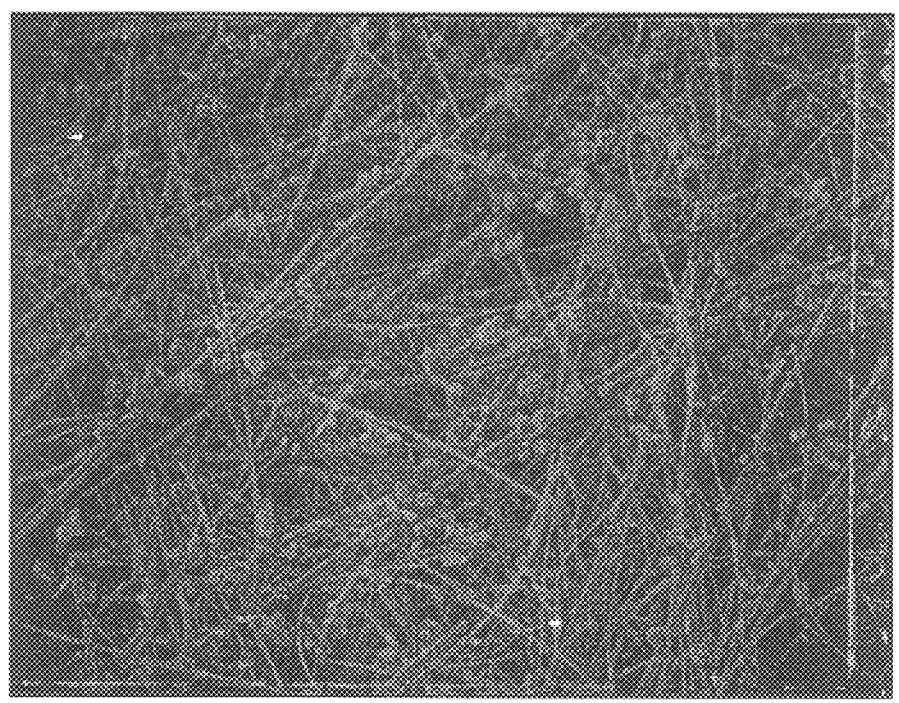
FIG. 2A is a scanning electron microscopy photograph of a filter treated with the antimicrobial agent of the present invention.
Figure 2B:
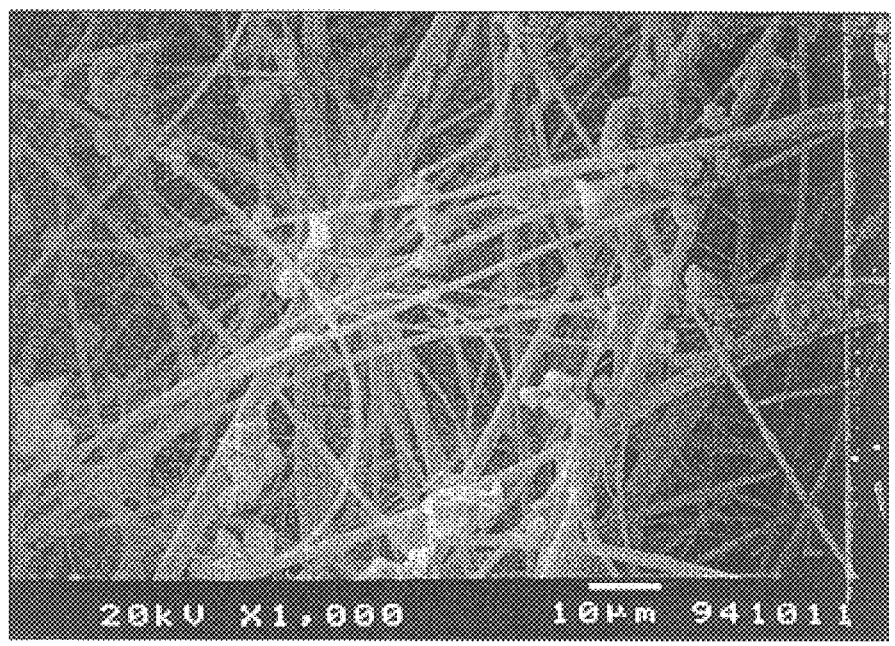
FIG. 2B is a scanning electron microscopy photograph of a filter treated with the antimicrobial agent of the present invention.

The present invention relates to a method of controlling microbial growth on a material. The method includes applying to the material an antimicrobial agent containing colloid particles having one or more ligands having antimicrobial properties.

"Antimicrobial" describes the killing of, as well as the inhibition of, the growth of bacteria, yeast, fungi, algae, viruses, and mold.

Ligands having antimicrobial properties include compounds having reactive inorganic cations, particularly those which have one or more electrons available for chemical reactions (i.e. transition metals) and compounds containing organic cations known to have bactericidal activity, for example, the antimicrobial effects of quaternary ammonium compounds, iodophor compounds, phenolics, alcohol, chlorine, peroxides, aldehydes and metals have been well documented. *Disinfection, Sterilization and Preservation,* 4th ed., Lea and Fabiger, Philadelphia (1991), which is hereby incorporated by reference. Ligands having antimicrobial properties which are particularly desirable for use as ligands in the present invention include quaternary ammonium compounds, transition metals, organo metallic compounds, perchlorates, charged halogen-containing compounds, charged organic peroxides, ionic polymers, ionic surfactants, and mixtures thereof. Especially desirable quaternary ammonium compounds include hexadecyltrimethyl ammonium bromide, trimethylphenyl ammonium chloride, and mixtures thereof. Especially desirable transition metals include copper, iron, manganese, zinc, silver, mercury, and mixtures thereof.

Any inorganic material exhibiting a combination of high surface area and a substantial ion exchange capacity, such as natural and synthetic clay minerals, are useful as colloid particles in the present invention. Preferred inorganic materials have surface areas ranging from 50–1000 $m^2$/gm, with surface areas of 500–800 $m^2$/gm being especially desirable. Useful synthetic types of clay include a synthetic hectorite, which is a layered hydrous magnesium silicate, such as Laponite® (Southern Clay Products, Gonzales, Tex.), a synthetic mica-montmorillonite, such as Barasym®, (Baroid Division, NL Industries, Houston, Tex.) and mixtures thereof. Useful natural types of clay include swelling clays such as aliettite, beidellite, nontronite, saponite, sauconite, stevensite, swinefordite, volkonskoite, yakhontovite, hectorite, montmorillonite (such as BP colloid), bentonite, and mixtures thereof. Other useful materials (both synthetic and mineral) include, but are not limited to, zeolites, illite, chlorite, kaolinite, hydrotalcite, talc, halloysite, sepiolite, and palygorskite. Typically, the colloid particles of the present invention have a mean diameter of 1 nm to 1000 microns, with mean diameters of less than 2 microns being preferred.

In their unmodified state, clays have little deleterious effect on bacteria. Clay minerals typically have monovalent or divalent inorganic cations on the external and internal surfaces of the layer structure materials. When these cations are exchanged with ligands having antimicrobial properties, antimicrobial properties are imparted to the clay. The modified clays can be applied to substrates in the form of a surface coating or can be used as additives to the material to impart antimicrobial properties to the surface and the body of the material, respectively. Alternatively, the unmodified clay can be applied to a surface in the form of a surface coating, followed by contact with the ligand having antimicrobial properties. The inorganic cations of the clay are then exchanged with the ligand having antimicrobial properties. Thus, antimicrobial properties are imparted to the surface.

Clays particularly useful as colloid particles in the present invention are members of the smectite clay mineral group which are distinguished by a large surface area ("S"), the ability to exchange cations, specified by the cation exchange capacity ("C.E.C."), and by the ability to swell in the presence of water and a variety of organic liquids, specified by the thickness of the clay layers as revealed by X-ray diffraction. Smectite clay minerals are layer structures which have a net negative charge as the result of substitutions of different cations within the individual mineral sheets. The high surface areas of these materials results from three factors: 1) the small particle size which creates a large external surface area, 2) the ability of the clay layers to expand by incorporating between adjacent layers water and various organic liquids which create a large internal surface area and 3) the plate-like morphology of the colloid particles. The negative charge on the individual layers is balanced by cations, such as sodium, calcium, and magnesium, which are adsorbed onto both the external and internal surfaces of the clay layers.

Examples of specific types of clays from the smectite mineral group include: hectorite ("SHCa-1", the Source Clay Minerals identification code) (provided by Source Clay Minerals Repository, University of Missouri, Columbia, Mo.) with a C.E.C.=43.9 meq/100 gms and S=63.2 $m^2$/gm; Cheto montmorillonite ("SAz-1") with a C.E.C.=120 meq/100 gms and S=97.4 $m^2$/gm; Washington montmorillonite ("SWa-1"); Wyoming montmorillonite ("SWy-2") with a C.E.C=76.4 meq/100 gms, S=31.8 $m^2$/gm; Laponite® RD with a C.E.C.=73 meq/100 gms and S=330 $m^2$/gm; and Laponite® RDS with a C.E.C.=73 meq/100 gms and S=360 $m^2$/gm.

To produce the antimicrobial agent of the present invention, the colloid particles, either free or previously bound to a surface, are subjected to ion exchange reactions whereby one or more ligands having antimicrobial properties displace the normal endogenous inorganic cations or anions of the colloid particles. An important feature of this invention is that the modifying ligands are retained by the mineral surfaces even after exhaustive washing. Thus, the efficacy of the modified colloid particles to act as antibacterial agents is not readily lost by leaching.

Specifically, the preparation of the antimicrobial agent is based on the process of ion exchange within the colloid particle. For example, clays have exchangeable cations such as calcium, magnesium, potassium, sodium, and hydrogen on their internal and external surfaces. The cations on the clay mineral surfaces balance the net negative charge that occurs in clay minerals. Two adjacent negatively charged clay layers are held together by the presence of the cations situated between the layers. A typical clay particle can consist of from two to hundreds of such layers, all held together by the electrostatic bonds formed between the cations and the negatively charged surface of the clay layers. This bonding, although strong enough to keep the layers together, is much weaker than the bonding between the atoms that form the layers. This weaker bonding between the layers plus the strong attraction of the interlayer cations for water allows the entrance of water and other molecules into the interlayer space. The endogenous inorganic interlayer cations will be displaced by other inorganic or organic cations contained in the liquid. Thus, if clay particles are suspended in a liquid dispersant containing cations, such as one or more ligands having antimicrobial properties, there is an exchange of the endogenous inorganic interlayer cations of the clay for the cations in the liquid dispersant. Accordingly, these cations are referred to as exchangeable cations. It should also be noted that some colloid minerals have a net positive charge and in such a case, the exchangeable ions would be anions.

In the case of organic cations, in accordance with the present invention, a quantity of antimicrobial ligand of up to 200% of the C.E.C. can be achieved for loading the colloid particles. Although not meaning to be bound by theory, it is believed that this high loading is achieved due to the bonding of the one or more ligands having antimicrobial properties to other ligands having antimicrobial properties. More particularly, in the present invention, all surface and interlayer cations are replaced by one or more ligands having antimicrobial properties in an amount equivalent to 100% of the cation exchange capacity of the colloid particles. Further, other ligands having antimicrobial properties then bond to these ligands, such that a loading of an excess of and up to 200% of the cation exchange capacity of the colloid particles is achieved. The organic cation present in excess of the C.E.C. is probably attached to the organo-clay by interactions between the cation exchanged organic material and an organic salt (U.S. Pat. No. 4,365,030 to Oswald, et al., which is hereby incorporated by reference).

To produce the antimicrobial agent, preferably, from 0.1 to 10 wt % of colloid particles, such as clay, is mixed with the liquid dispersant. The liquid dispersant contains sufficient ligand to satisfy fully or partially the ion exchange capacity of the mineral colloid and to form a suspension containing the desired ligand having antimicrobial properties. The liquid dispersant is typically water, but it can be any liquid dispersant. The suspension is then thoroughly mixed and held for up to 24 hours at from 45° to 100° C. The suspension is then centrifuged, decanted, and water washed three times, preferably with distilled water. It is especially desirable to expose the colloid particles to fresh solution three times to ensure maximum loading of the antimicrobial ligand. The colloid particles may be exposed to different types of ligands in order to bind two or more different types of ligands to the colloid particles. Preferably, a loading of up to 200% of the cation exchange capacity is achieved. For instance, if Wyoming montmorillonite ("SWy-2") is immersed in an aqueous solution of hexadecyltrimethyl ammonium bromide ("HDTMA"), the organic cations of the HDTMA will exchange for the inorganic cations of the clay and the clay surface will become antimicrobial.

The antimicrobial agent can be applied to a material surface to impart antimicrobial properties to the surface. The antimicrobial agent can be applied to the surface by any means, for example, by spraying, spreading, dipping, or brushing. As discussed above, the antimicrobial agent can be applied in a single step where the colloid particles having one or more ligands with antimicrobial properties are applied to the surface. Alternatively, a two step process can be used, where the colloid particles are applied to the surface followed by contacting the colloid particles with the one or more ligands having antimicrobial properties. The surface can be any surface which it is desired to make antimicrobial. Such surfaces include, but are not limited to, surfaces made of cellulose, fiberglass, plastics, metals, glass, ceramic, wood, leather, cloth, and painted surfaces.

The thickness of the applied coating can be varied depending upon the need. For example, when coating filters, ideally, a very thin coating of the antimicrobial agent should be applied. If the coating is too heavy, it is likely to block the filter pores and interfere with the filtering function. It is understood that one skilled in the art will be able to select the appropriate thickness for their use.

In a preferred embodiment, the antimicrobial agent of the present invention is applied to a filter material to impart antimicrobial properties to the filter. Coating the filter material with the modified antimicrobial clay can be achieved by various methods. Examples of useful methods of coating the filter material include 1) dipping the filter material into an aqueous suspension of the modified clay, 2) spraying the filter material with a suspension of the modified clay, or 3) by pre-adsorbing unmodified clay onto the filter material and then performing the cation exchange process by exposing the clay-treated filter material to an aqueous solution of the ligand having antimicrobial properties. The time of exposure of the filter material to the modified clay suspension can vary from a few seconds to hours, days or longer depending on the application. This process may be repeated to apply more antimicrobial ligand to the surface.

Once coated onto the surface in question, the antimicrobial agent of the present invention does not readily leach out, eliminating the need for repeated coatings. In addition, the ability of the antimicrobial agent to strongly bind to the coated surfaces indicates that no significant particulate material is given off from such surfaces. Typical applications include applying the antimicrobial agent on air and water filtration devices, air ductwork, and fan housings to prevent microbial growth. Examples of other surfaces which can be coated with the antimicrobial agent of the present invention includes aquarium filter material, automobile ventilation and air conditioner systems, bed sheets, blankets and bedspreads, buffer pads (abrasive and polishing), carpets and draperies, fiberfill for upholstery, sleeping bags, apparel, etc., where the fiber is cotton, natural down, nylon, polyester, rayon or wool, fiberglass ductboard, fire hose fabric, humidifier belts, mattress pads and ticking, underwear and outerwear, nonwoven disposable diapers, nonwoven polyester, outerwear apparel, disposable polyurethane foam cushions, polyurethane foam for household, industrial and institutional sponges and mops, polyurethane foam for packaging and cushioning in contact applications, polyurethane foam used as a growth medium for crops and plants, premoistened towelettes and tissue wipes, roofing materials—such as shingles, roofing granules, wood shakes, felt, stone and synthetic overcoats, sand bags, tents, tarpaulins, sails and ropes, athletic and casual shoes, shoe insoles, shower curtains, socks to provide residual self-sanitizing activity against athlete's foot fungus (i.e. *Trichophyton mentagrophytes*) on the sock, throw rugs, toweling made of 100 percent cotton, 100 percent polyester, and blends of the two fibers, toilet tank and seat covers, umbrellas, upholstery made of acetates, acrylics, cotton, fiberglass, nylon, polyester, polyethylene, polyolefins, polypropylene, rayon, spandex, vinyl and wool, vacuum cleaner bags and filters, vinyl paper or wallpaper, disposable wiping cloths that can be used for multiple purposes such as dusting or washing furniture, cars, walls, windows, floors, appliances, dishes, counter tops, etc., women's hosiery, and women's intimate apparel.

Alternatively, the antimicrobial agent can be mixed with a material to impart antimicrobial properties to the material. For example, the antimicrobial agent can be incorporated into plastics to impart antimicrobial properties to the plastic The plastic can be used to make a wide variety of products including medical items (such as catheters, blood lines, implants, thermometers, bandages, surgical dressings, surgical apparel, respirators), food packaging, drug and cosmetic packaging, eating utensils, shower curtains, bath mats and the like. Further, the antimicrobial agent may be added to grouts, cements, and concretes to prevent unsightly mold or mildew from growing in or on the grout, cement, and concrete, respectively. In addition, the antimicrobial agent is blended with other solid materials to produce materials such as sponges, toilet seats, rubber gloves, contact lenses, hearing aids, dusting powder, kitchen, bath, or laboratory shelf paper, carpet pads, pool covers, solar pool covers, cat litter, animal bedding, computer keyboard covers, computer keys, door knobs, tampons, sanitary napkins, dental chairs, dryer sheets, mops, and dishcloths to impart antimicrobial properties to those materials.

Likewise, the antimicrobial agent is blended with liquids or gels as a suspension to impart antimicrobial properties to the liquid or gel. For example, the antimicrobial agent can be added to water for use as a disinfecting agent for cleaning walls, floors, counters, and tabletops. It can also be mixed into cosmetics and into paints. At higher concentration levels, the antimicrobial agent can be mixed with a detergent and used as a surgical scrub. The antimicrobial agent can be mixed with paint or other coatings (such as polymers) and applied to surfaces to prevent growth of microbials. In addition, the antimicrobial agent can be added to the water in cooling towers or can be included in a coating that is used to coat the surfaces in cooling towers to kill or inhibit the growth of bacteria.

In addition, the antimicrobial agent of the present invention can be applied topically to both natural and synthetic fibers or can be incorporated directly into synthetic fibers during the manufacturing process. The fibers that can be used with the antimicrobial agent of the present invention include but are not limited to fibers made of wool, cotton, polyolefin, polyester, polyaramid, cellulose acetate, rayon, nylon, polystyrene, vinyls, acrylics, and polyurethanes.

The antimicrobial agent can be applied to the fiber or fabric by mixing it with a liquid such as water or other solvent or dispersant and then dipping, spraying or washing the fiber or fabric in the mixture. As discussed above, alternatively, the fiber or fabric could first be contacted with the unmodified clay followed by contact with the ligand having antimicrobial properties. Suitable solvents that can be used in either method to apply the antimicrobial agent include, but are not limited to, aliphatic and aromatic solvents such as alcohols, benzene, toluene, xylene, and hexane. After applying the mixture, the fiber or fabric will be coated with the antimicrobial agent. Therefore, when microorganisms come into contact with the fiber or fabric, the antimicrobial agent will kill or inhibit the growth of the microorganism.

Examples of the type of fiber or fabric products contemplated include, but are not limited to, surgical gauze, padding on wound dressings, mattress covers, crib covers, bassinet covers, sailboat sails, tents, draw sheets, cubicle curtains, tooth brushes, hair brushes, fabric wall covering, fabric base, fabric shower curtains, bath mats, athletic clothing such as underclothes, shirts, socks, shorts, pants, shoes and the like, and hospital clothing such as examination robes, physicians coats, and nurses uniforms.

The following examples are presented to further illustrate the invention.

EXAMPLES

Materials

The naturally occurring clays were obtained from Dr. William D. Johns, Director, the Source Clay Minerals Repository, University of Missouri, Columbia Mo. 65201. These materials are described in "Data Handbook for Clay Materials and other Non-metallic Minerals", by H. van Olphen and J. J. Fripiat (Pergamon Press, New York, 1979). The synthetic clays (Laponite® RDS and Laponite® RD) and the natural BP were obtained from Southern Clay Products Inc., Gonzales Tex.

Example 1
Preparation of Antimicrobial Agent and Its Application to a Surface in a Single Step An antimicrobial HEPA filter/mineral colloid product can be achieved several ways. A preferred method is to perform a cation ion exchange of a selected clay to produce a modified clay. For instance, 25 grams of Laponite® RDS synthesized clay was added to a 600 ml bottle containing a solution of the desired ligand having antimicrobial properties. The solution concentration can vary from nearly saturated to very weak. One can adjust the amount of ligand so that there is just enough ligand present to do a complete exchange as determined by the cation exchange capacity. To achieve maximum loading in excess of the C.E.C., a minimum of-three exposures to fresh solution is recommended. After an addition of antimicrobial solution, the suspension was thoroughly mixed and placed in a warm (about 60° C.) oven overnight. This was followed by centrifugation and decanting of the supernatant liquid. For maximum loading, this procedure was repeated two more times, each time beginning with the addition of fresh antimicrobial solution. The final step was distilled water washing of the antimicrobial clay three times. The sample of antimicrobial agent was then freeze dried and stored for subsequent use. The antimicrobial agent was then added to water to prepare a 0.1 to 5% (wt/vol) suspension. The HEPA filter was placed into the suspension and kept there for 30 minutes. After removing the coated HEPA filter from the suspension it was rinsed rigorously and dried.

Example 2
Application of Antimicrobial Agent to a HEPA Filter in Two Steps

In the second method of preparation, untreated clay was first adsorbed to the HEPA filter and the cation exchange was then carried out. A suspension of SWy-2 smectite clay was prepared. The maximum percent of clay used to form a suspension was determined by the clay itself—in this case, no more than 4% wt/vol clay was used. If more were used, the suspension would form a gel. Typically, from 0.1 to 1 wt % suspension is recommended. The filter was dipped into the suspension for 30 minutes. The clay covered filter was then dipped into a cationic solution of from 0.01 to 0.1 M of HDTMA to produce a filter coated with an antimicrobial agent.

Example 3
Deposition of Modified Clay Minerals on HEPA Filters

Experiments were designed to demonstrate that the modified clay material could be coated on the filter fibers so that any bacteria in physical contact with the filter would also contact one or more clay particles.

The antimicrobial colloid were prepared as follows. One sample was prepared by adding 20 grams of Wyoming montmorillonite ("SWy-2") to 100 mls of 0.1M HDTMA aqueous solution. This suspension was placed into a 58° C. oven overnight. The sample was then removed from the oven and separated from the solution by centrifugation. Fresh aqueous solution containing HDTMA was then added to the sample, and the mixture was returned to the oven, heated overnight, and separated by centrifugation. This procedure was repeated a third time. The sample was then separated from the solution and washed with distilled water three times, returned to the oven overnight, separated from wash water, frozen, and then freeze dried.

A second sample was prepared in the same manner with the exception of using 10 grams of the synthetic Laponite® RD clay and treating it with 100 mls of a 0.1 M aqueous solution of $CuCl_2$.

Small pieces of high efficiency particulate arrest ("HEPA") filter material were placed in each of the suspensions for a period of 30 minutes, after which the paper was removed. The suspensions were made from the HDTMA loaded clay and the Cu loaded clay, prepared as described above, by adding 2 grams of the antimicrobial agent to 200 ml of distilled water and stirring while the HEPA filter was in contact with the suspension. Some filter paper pieces were dried directly and others were rinsed in distilled water before drying. The appearance and distribution of the clay on the filter were determined by scanning electron microscopy. Two morphologies were observed. In one, the montmorillonite clay occurred as small (micron sized) irregular to spherical particles, more or less uniformly distributed over the surface of the filter (shown in FIGS. 1A and 1B). FIG. 1A is the HEPA filter with no treatment at a magnification of 3500 times. FIG. 1B is a HEPA filter treated with 0.5% SWy-2/HDTMA at a magnification of 200 times. The second morphology (as shown in FIGS. 2A and 2B, which show HEPA filters treated with 0.5% Laponite®/Cu at a magnification of 350 times and 1000 times, respectively) showed thin sheets or films of clay coating the fibers and stretching between the fibers. This second morphology was most often observed for the clay types Laponite® RD and RDS and hectorite. The coverage of both samples appeared to be adequate so that a micron sized bacterium would physically contact one or more modified clay particles. Further, there appeared to be no significant blockage of the pore system in the filter paper.

Calculation of the amount of clay actually deposited by this treatment on the filter material indicated that enough clay was added to the filter to provide a thickness of 1.3 microns, assuming uniform coverage.

Example 4
Antimicrobial Effects of Modified Clays when Mixed with a Material The ability of various clays having ligands with antimicrobial properties to prevent microbial growth was tested using an environmental microbe source obtained from activated sewage sludge. The activated sewage sludge was prepared as described in ASTM Method D5209-92.

Figure 3A:
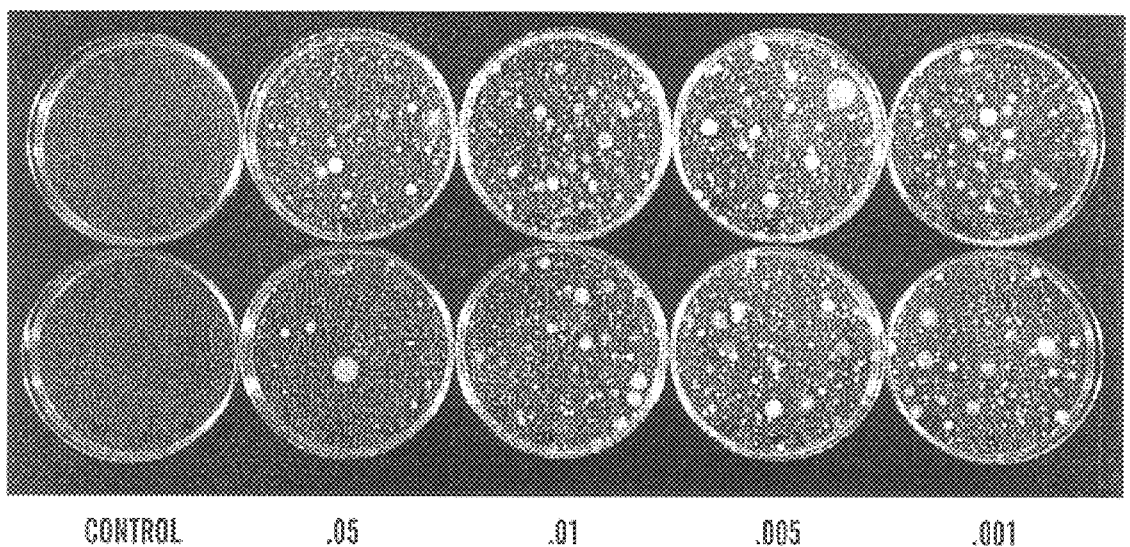
FIG. 3A is a photograph of a plate assay showing a comparison of antimicrobial activity of the antimicrobial agents of the present invention.
Figure 3B:
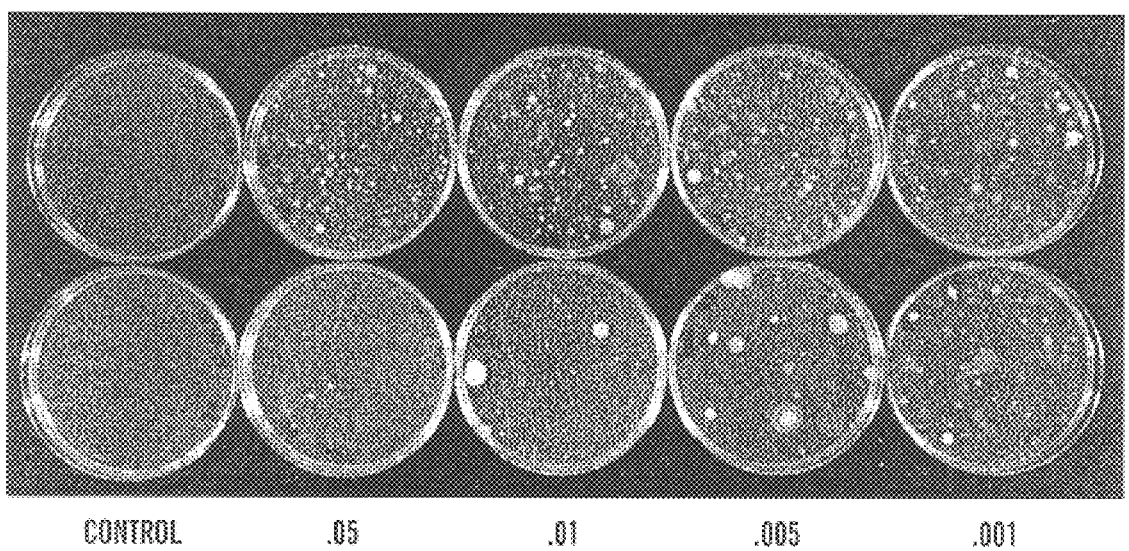
FIG. 3B is a photograph of a plate assay showing a comparison of antimicrobial activity of the antimicrobial agents of the present invention.

The standard plate count assay described by the EPA Microbiological Methods for Monitoring the Environment (EPA 600/8-78-017) was used to determine the number of colony forming units ("cfu") present in the activated sludge. The antimicrobial effects of the various clays and modified clays were assessed using the following modification of the EPA plating method. Clays and modified clays were added directly to the molten agar and mixed for 1 hour. This mixture was maintained in molten form in a 48° C. water bath until use. One tenth milliliter (0.1 ml) of microbial incubation suspension, prepared by diluting the activated sewage sludge with medium to give 200–250 cfu, was added to the plate and 15 ml of the agar/test substance mixture pipeted onto the plate. This was mixed by swirling the plates. Triplicate plates for each sample were prepared, incubated at 37° C. in a humidified atmosphere for two days, and counted as in the EPA method. Two typical sets of plates are shown in FIGS. 3A and 3B. The plate assay results for antimicrobial activity of copper-modified Laponite® RD (upper photograph) are compared to HDTMA-modified Laponite® RD (lower photograph) in FIGS. 3A and 3B. In both cases, the tested concentration (% wt/vol) is given in the center of the Figure for the respective plates of unmodified Laponite® RD (top row of both photographs) and modified Laponite® RD (bottom row of both photographs). The concentration decreases from left to right in the Figures. The unmodified Laponite® RD had no effect on microbial colony counts. A decreased number of microbial colonies are seen with increasing concentrations of both copper- and HDTMA-modified Laponite® RD, and the HDTMA-modified Laponite® RD was more effective than the copper-modified Laponite® RD. Inhibition of microbial growth is clearly demonstrated by the reduction of the number of colonies on the plates. Control plates with no added microbes and with microbes but no additives (not shown) provide a negative control and a total count of the microbe population inoculated on the plates. This experiment provided an efficient testing of a wide variety of microbes at one time, and has relevance to the real world application for devices proposed for applications for this technology. These experiments indicated that the efficacy of the modified clays depends upon the type of clay as well as the modifying ligand.

The modified clays were prepared as follows. A series of natural and man-made clay minerals was modified by the exchange of cations with transition metals and cationic organic antimicrobials. A summary of the treated clays and the ligands bound to the clays surfaces is provided in Table I:

TABLE I

Figure 4:
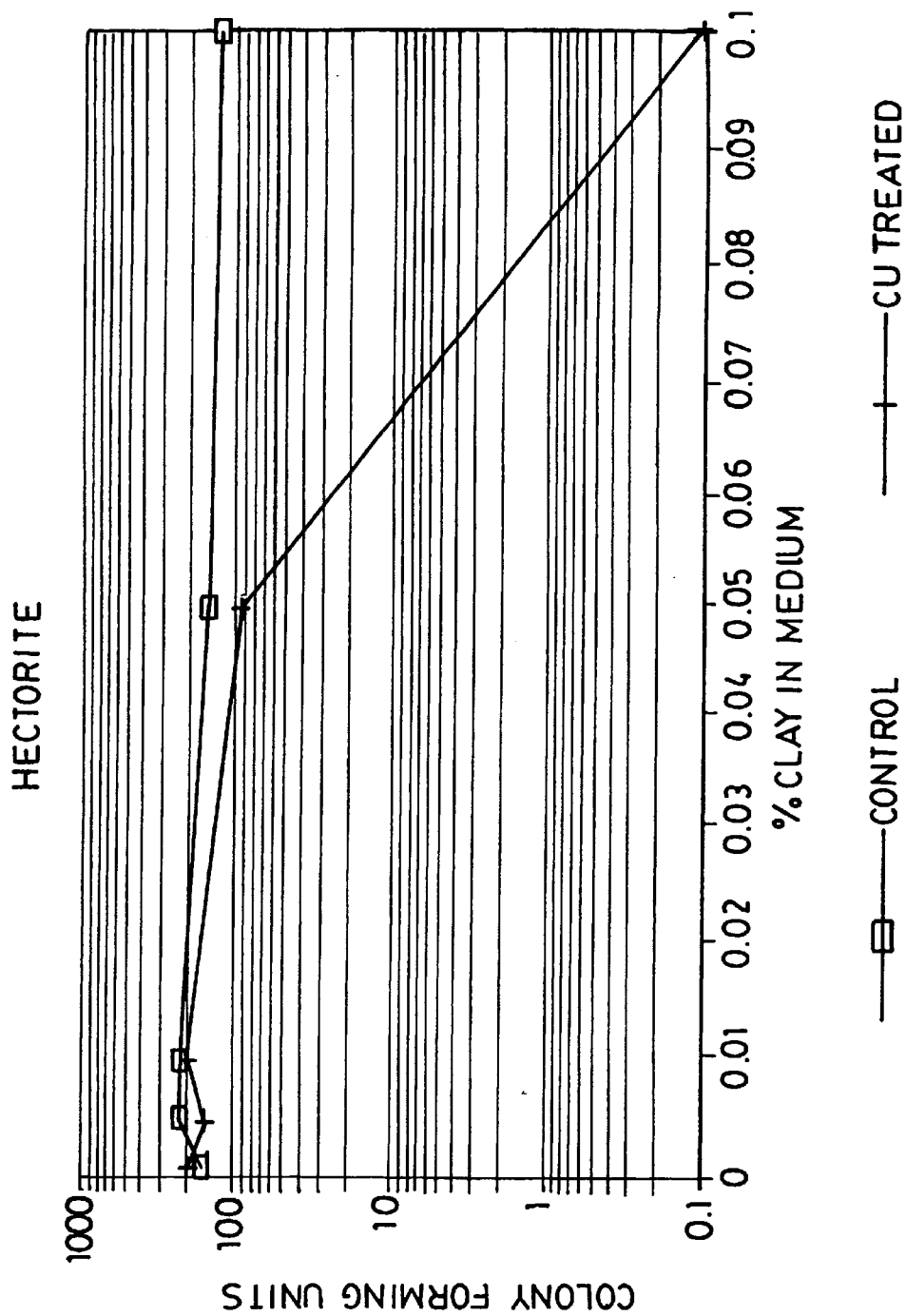
FIG. 4 is a plot of colony forming units versus untreated hectorite and hectorite treated with the antimicrobial agent of the present invention.

| Clay | Metal | | | | Organics | | |
|---|---|---|---|---|---|---|---|
| Hectorite | Cu | | Mn | Zn | HDTMA | | |
| Montmorillonite (SAz) | Cu | Fe | Mn | Zn | HDTMA | TMPA | 4AP |
| Montmorillonite (SWy) | Cu | Fe | Mn | Zn | HDTMA | TMPA | 4AP |
| Montmorillonite (SWa) | Cu | Fe | Mn | Zn | HDTMA | TMPA | 4AP |
| Laponite ® RD | Cu | Fe | | Zn | HDTMA | | | where
HDTMA is hexadecyltrimethyl ammonium bromide
TMPA is trimethylphenyl ammonium chloride
4AP is 4-aminophenolhydrochloride All of the clay minerals studied underwent exchange reactions whereby the antimicrobial ligand shown in Table I displaced the normal endogenous cations and was retained by the mineral surfaces even after exhaustive washing. Of the metals tested, copper-modified clays offered the greatest antimicrobial effect of all of the transition metals studied. The order of efficacy was Cu>Mn>Zn>Fe. The antimicrobial efficacy for copper-modified natural clays was in the order hectorite>montmorillonite. Different varieties of the montmorillonite clay exhibited different efficacy with the order being SAz>SWa>SWy. A typical comparison of Cu-modified hectorite with untreated hectorite clay is shown in FIG. 4.

Of the organic antimicrobials which were tested, HDTMA provided the greatest antimicrobial activity of any antimicrobial modifier studied. The efficacy of HDTMA modified Laponite® RD was approximately 5 to 10 times that of Cu modified Laponite® RD.

Figure 5:
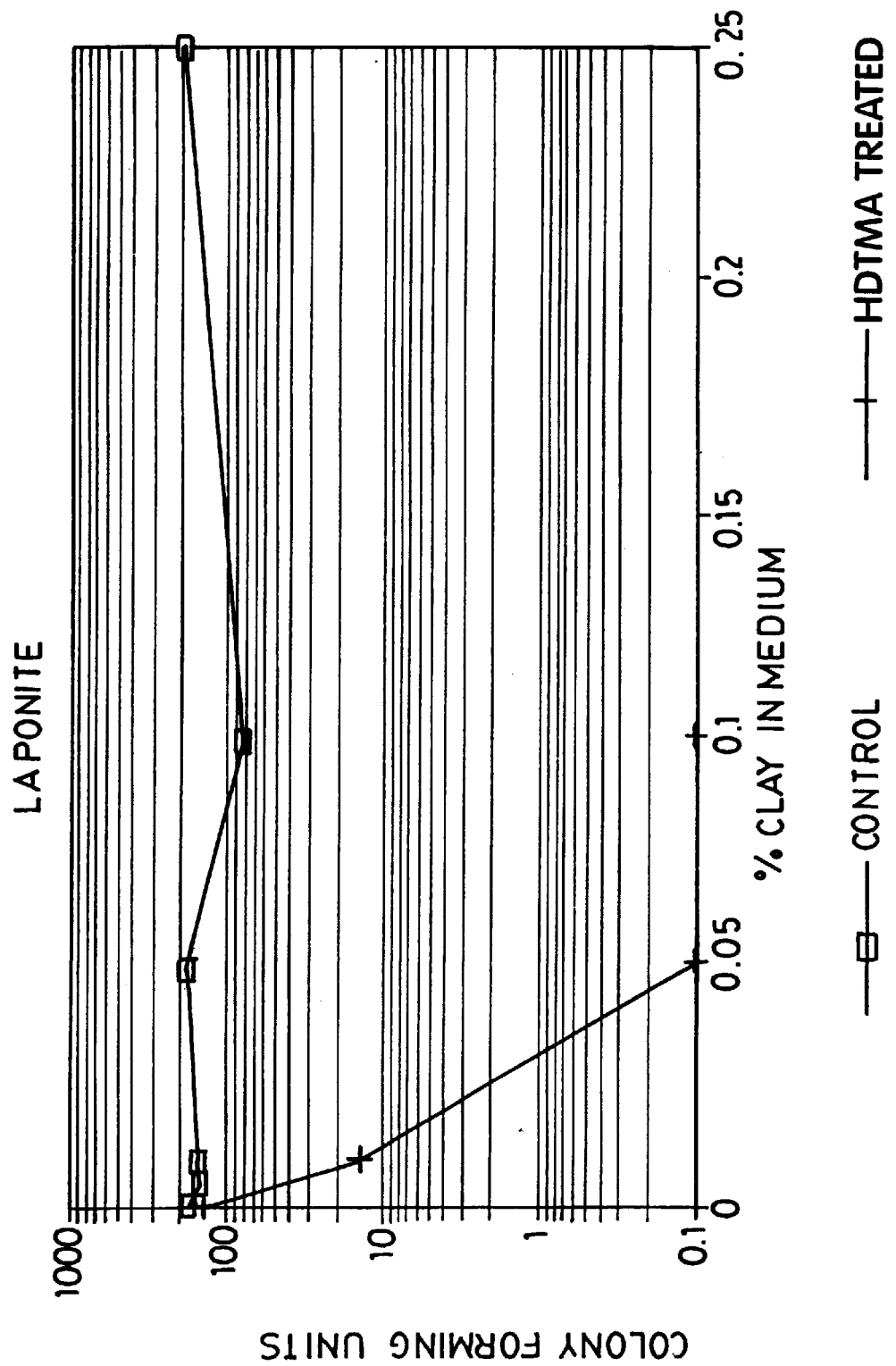
FIG. 5 is a plot of colony forming units versus untreated Laponite® and Laponite® treated with the antimicrobial agent of the present invention.

The synthetic clay, Laponite® RD, displayed similar or slightly higher efficacy when modified by either HDTMA or Cu when compared to the modified hectorite clay. Laponite® RD provided significant advantages over the natural clay minerals with regard to its purity, consistency of chemical composition, particle size, and ability to coat filter material with considerably less clumping than the natural clays. The antimicrobial properties of modified Laponite® RD were greater than the most active modified natural clays, as shown in FIG. 5 (and compared to FIG. 4).

Figure 6:
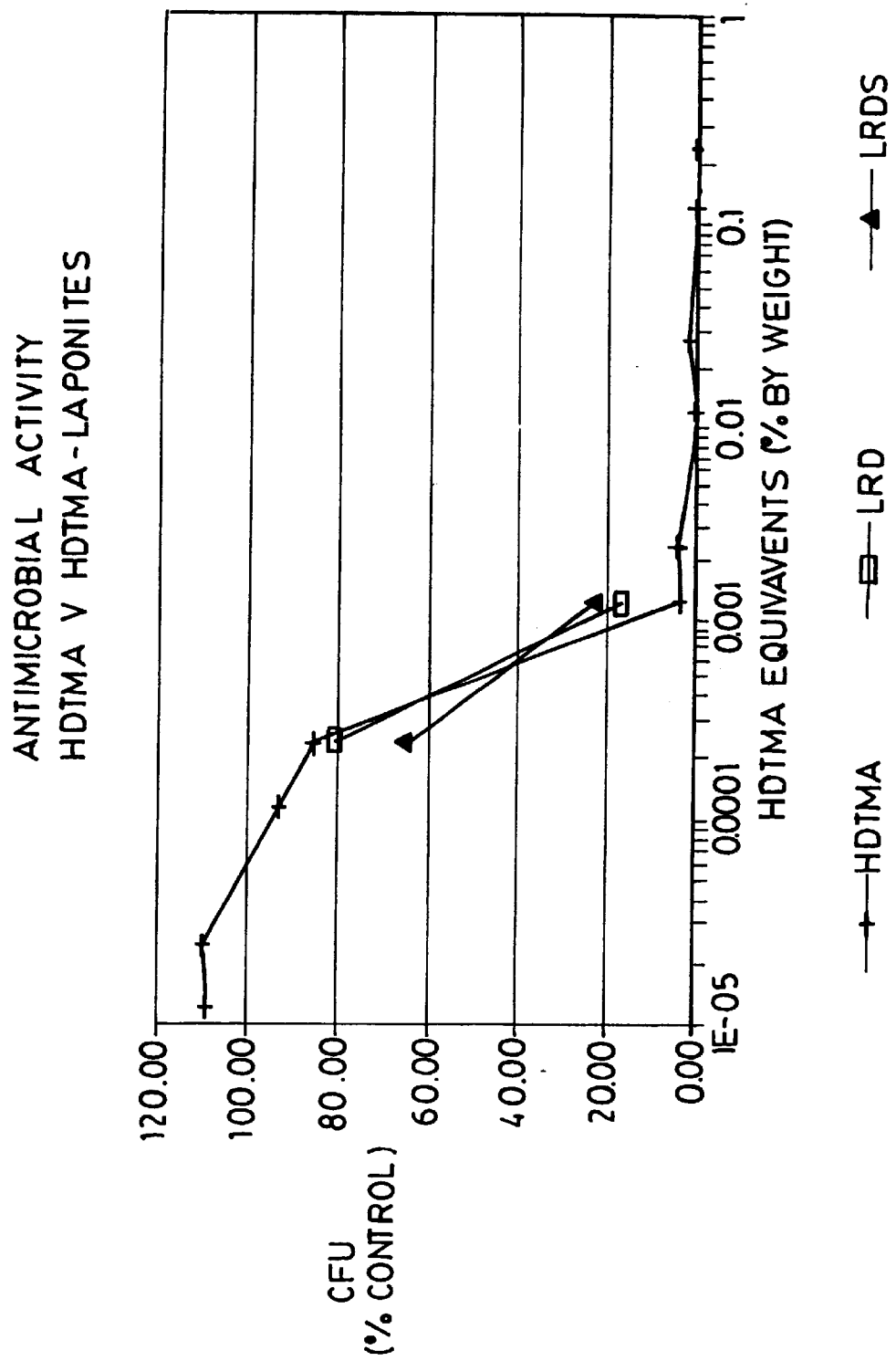
FIG. 6 is a plot of colony forming units versus HDTMA alone and HDTMA bound to Laponite® RD and Laponite® RDS.

Example 5
Antimicrobial Potency of Ligand-Modified Laponites® Compared to Pure Antimicrobial Ligand The antimicrobial potency of HDTMA and HDTMA-modified Laponite® RD and Laponite® RDS was compared using the antimicrobial assay methods described in Example 4. HDTMA was tested over a concentration range of $1.2 \times 10^{-5}$ to $1.2 \times 10^{-1}$% by weight. Both HDTMA modified Laponite® RD and RDS were tested at $1.2 \times 10^{-3}$ and $2.4 \times 10^{-4}$% HDTMA equivalents by weight. As seen in FIG. 6, both HDTMA Laponite® RD and HDTMA Laponite® RDS had similar antimicrobial potency, which was indistinguishable from HDTMA alone. Thus, binding of HDTMA to the mineral colloid has no observable detrimental effect on its antimicrobial potency.

Example 6
Antimicrobial Potency of Ligand-Modified Laponite® and BP with HDTMA Loading The effects of clay loading with an antimicrobial were determined under conditions which achieved varying amounts of antimicrobial on the clay. Both a natural clay, BP, a natural montmorillonite clay and a synthetic clay, Laponite® LRD, were studied. Both clays first were treated with an HDTMA concentration equivalent to the cation exchange capacity for the particular clay. The treatment was repeated twice for a total of three treatments. The treated clays received three warm water washings and were freeze dried. The amounts of HDTMA associated with the clays after each of the treatments was estimated by a microwave ashing procedure. Samples were then tested for antimicrobial activity using a *Pseudomonas aeruginosa* assay in which the organism was spread on the surface of the plates at an inoculation density of 100 to 200 cfu per plate, and incubated overnight at 37° C.

The ashing results clearly show that a single treatment of Laponite® RD at a concentration equivalent to the C.E.C. results in an amount of HDTMA bound which was essentially equivalent to the C.E.C. for the clay. Multiple treatments of the Laponite® RD clay with HDTMA resulted in the binding of an amount of HDTMA that exceeds the CEC for that clay. In the clay treated two times, the loading of HDTMA was equal to 181% of the C.E.C. for Laponite® RD. When treated three times, the HDTMA loading increased to 200% of the C.E.C. The comparable values for the BP clay were 100% of the C.E.C. for the single treatment and 187% of the C.E.C. for the clay treated three times.

Figure 7:
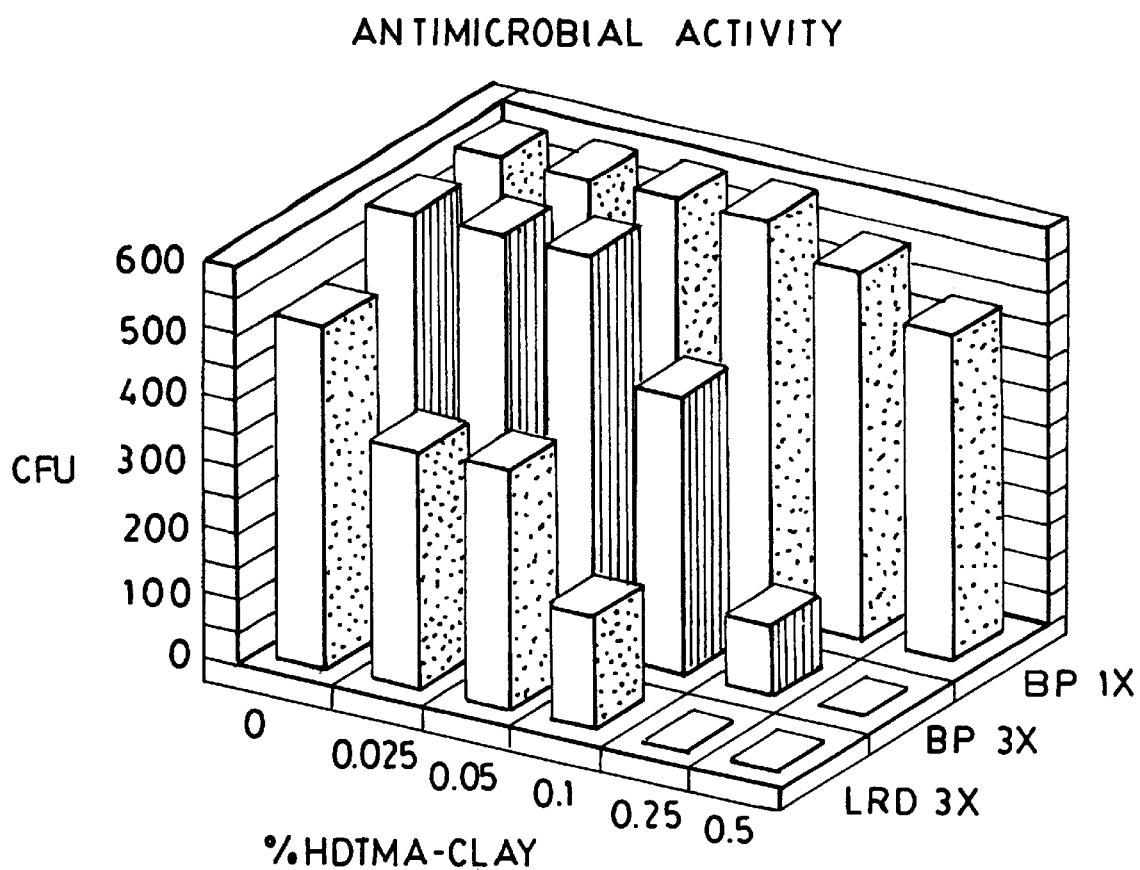
FIG. 7 is a plot of colony forming units versus clay samples of HDTMA bound to Laponite® RD and HDTMA bound to BP with different HDTMA loadings.

The increase in the amount of HDTMA associated with the clays correlates with an enhanced antimicrobial effect for both the natural and synthetic clay. This is shown in FIG. 7. A single treatment of BP with HDTMA bound thereto (i.e. having ligand which fulfilled 100% of the CEC) resulted in no antimicrobial activity until the concentration of the treated clay exceeded 0.25% (w/v) of the medium. The BP treated three times with HDTMA (i.e. having ligand which fulfilled 187% of the CEC) had antimicrobial activity beginning at 0.1%. Laponite® LRD treated three times with HDTMA (i.e. having ligand which fulfilled 200% of the CEC) had antimicrobial activity at all concentrations tested including 0.025%. This clearly demonstrates the enhanced antimicrobial activities imparted to clays having ligand bound thereto, where the quantity of ligand attached to the clay is up to 200% of the CEC of the clay.

Example 7
Leachability of Antimicrobial Modifier from Filters

*Pseudomonas aeruginosa* (ATCC 27853) was obtained from the American Type Culture Collection (Rockville, Md.). The organism was plated on Nutrient Broth Agar (Difco Laboratories, Detroit, Mich.) at $10^8$ bacteria per plate, and incubated 24 hours at 37° C. to establish a confluent layer of Pseudomonas on the plate.

Laponite® RD modified with HDTMA was dip coated onto 1 cm diameter HEPA filters from suspensions containing from 0.5% to 8.6% Laponite® RD/HDTMA. Filters were then washed exhaustively. Treated filters were placed on the layer of *Pseudomonas aeruginosa* and incubated overnight. A clear zone surrounding the filter would indicate the migration of the antimicrobial from the filter.

No clear zone was detected for any of the four dip concentrations of filters studied. At the same time, there was no visible overgrowth of the filters by the bacteria. Similarly treated filters placed on nutrient broth agar inoculated simultaneously with $10^8$ bacteria per plate and similarly incubated revealed no zones of growth inhibition. Thus, HDTMA appeared to maintain its antimicrobial activity on the filter without migrating from the filter.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method of controlling microbial growth on a material, said method comprising:
   applying to the material an antimicrobial agent comprising:
   colloid particles having an ion exchange capacity and having attached a quantity of one or more ligands with antimicrobial properties, wherein the quantity of ligand attached to the colloid particles is in excess of 100% and up to 200% of the ion exchange capacity of the colloid particles.

2. A method according to claim 1, wherein the colloid particles are selected from the group consisting of natural clays, synthetic clays, zeolites, hydrotalcite, kaolinite, talc, halloysite, sepiolite, illite, chlorite, and palygorskite.

3. A method according to claim 2, wherein the colloid particles are synthetic clay selected from the group consisting of layered hydrous magnesium silicate, synthetic mica-montmorillonite, and mixtures thereof.

4. A method according to claim 2, wherein the colloid particles are natural clays selected from the group consisting of hectorite, aliettite, beidellite, nontronite, saponite, sauconite, stevensite, swinefordite, volkonskoite, yakhontovite, montmorillonite, bentonite, and mixtures thereof.

5. A method according to claim 1, wherein the ligand is selected from the group consisting of quaternary ammonium compounds, antimicrobial metals, organo metallic compounds, perchlorates, charged halogen-containing compounds, charged organic peroxides, ionic polymers, ionic surfactants, and mixtures thereof.

6. A method according to claim 5, wherein the ligand is a quaternary ammonium compound selected from the group consisting of hexadecyltrimethyl ammonium bromide, tri-methylphenyl ammonium chloride, and mixtures thereof.

7. A method according to claim 6, wherein the one or more ligands comprise at least two ligands.

8. A method according to claim 7, wherein the at least two ligands are different.

9. A method according to claim 5, wherein the antimicrobial metal is a transition metal selected from the group consisting of copper, iron, manganese, zinc, silver, mercury, and mixtures thereof.

10. A method according to claim 1, wherein the material is a surface to which the antimicrobial agent is applied.

11. A method according to claim 10, wherein the colloid particles having one or more ligands having antimicrobial properties are applied to the surface in a single step.

12. A method according to claim 10, wherein the surface is selected from the group consisting of cellulose, fiber glass, plastics, metals, glass, wood, leather, ceramic, cloth, and painted surfaces.

13. A method of claim 12, wherein the surface is filter.

14. A method according to claim 1, wherein the colloid particles have a mean diameter of 1 nm to 1000 μm.

15. A method according to claim 14, wherein the colloid particles have a mean diameter of 1 nm to 2 μm.

16. A method of controlling microbial growth in a material, said method comprising:

mixing with the material colloid particles having an ion exchange capacity and having attached one or more ligands having antimicrobial properties, wherein the one or more ligands attached to the colloid particles is in a quantity in excess of 100% and up to 200% of the ion exchange capacity of the colloid particles.

17. A method according to claim 16, wherein the colloid particles are selected from the group consisting of natural clays, synthetic clays, zeolites, hydrotalcite, kaolinite, talc, halloysite, sepiolite, illite, chlorite, and palygorskite.

18. A method according to claim 17, wherein the colloid particles are synthetic clay selected from the group consisting of layered hydrous magnesium silicate, synthetic mica-montmorillonite, and mixtures thereof.

19. A method according to claim 17, wherein the colloid particles are natural clays selected from the group consisting of hectorite, aliettite, beidellite, nontronite, saponite, sauconite, stevensite, swinefordite, volkonskoite, yakhontovite, montmorillonite, bentonite, and mixtures thereof.

20. A method according to claim 17, wherein the ligand is selected from the group consisting of quaternary ammonium compounds, organo metallic compounds, ionic polymers, and ionic surfactants, and mixtures thereof.

21. A method according to claim 20, wherein the ligand is a quaternary ammonium compound selected from the group consisting of hexadecyltrimethyl ammonium bromide, trimethylphenyl ammonium chloride, and mixtures thereof.

22. A method according to claim 21, wherein the one or more ligands comprise at least two ligands.

23. A method according to claim 22, wherein the at least two ligands are different.

24. A method according to claim 21, wherein the antimicrobial agent is blended with other solid materials or with liquids as a suspension.

25. A method according to claim 16, wherein the colloid particles have a mean diameter of 1 nm to 1000 $\mu$m.

26. A method according to claim 25, wherein the colloid particles have a mean diameter of 1 nm to 2 $\mu$M.

27. An antimicrobial surface coated with colloid particles having an ion exchange capacity and having attached a quantity of one or more ligands having antimicrobial properties, wherein the quantity of ligand attached to the colloid particles is in excess of 100% and up to 200% of the ion exchange capacity of the colloid particles.

28. An antimicrobial surface according to claim 27, wherein the colloid particles are selected from the group consisting of natural clays, synthetic clays, zeolites, hydrotalcite, talc, halloysite, sepiolite, illite, chlorite, kaolinite, and palygorskite.

29. An antimicrobial surface according to claim 27, wherein the colloid particles are synthetic clay selected from the group consisting of layered hydrous magnesium silicate, synthetic mica-montmorillonite, and mixtures thereof.

30. An antimicrobial surface according to claim 28, wherein the colloid particles are natural clays selected from the group consisting of hectorite, montmorillonite, aliettite, beidellite, nontronite, saponite, sauconite, stevensite, swinefordite, volkonskoite, yakhontovite, and mixtures thereof.

31. An antimicrobial surface according to claim 28, wherein the ligand is selected from the group consisting of quaternary ammonium compounds, transition metals, organo metallic compounds, perchlorates, charged halogen-containing compounds, charged organic peroxides, ionic polymers, ionic surfactants, and mixtures thereof.

32. An antimicrobial surface according to claim 28, wherein the ligand is a quaternary ammonium compound selected from the group consisting of hexadecyltrimethyl ammonium bromide, trimethylphenyl ammonium chloride, and mixtures thereof.

33. An antimicrobial surface according to claim 32, wherein the one or more ligands comprise at least two ligands.

34. An antimicrobial surface according to claim 33, wherein the at least two ligands are different.

35. An antimicrobial surface according to claim 28, wherein the ligand is a transition metal selected from the group consisting of copper, iron, manganese, zinc, silver, mercury, and mixtures thereof.

36. An antimicrobial surface according to claim 27, wherein the colloid particles have a mean diameter of 1 nm to 1000 $\mu$m.

37. An antimicrobial surface according to claim 36, wherein the colloid particles have a mean diameter of 1 nm to 2 $\mu$m.

38. An antimicrobial surface according to claim 28, wherein the surface is selected from the group consisting of cellulose, fiber glass, plastics, metals, glass, wood, leather, ceramic, cloth, and painted surfaces.

39. An antimicrobial surface according to claim 38, wherein the surface is a filter.

40. A material to which antimicrobial properties have been imparted, wherein said material contains colloid particles having an ion exchange capacity and having attached one or more ligands with antimicrobial properties, wherein the one or more ligands attached to the colloid particles is in a quantity in excess of 100% and up to 200% of the ion exchange capacity of the colloid particles.

41. A material according to claim 40, wherein the colloid particles are selected from the group consisting of natural clays, synthetic clays, zeolites, hydrotalcite, talc, halloysite, sepiolite, illite, chlorite, kaolinite, and palygorskite.

42. A material according to claim 41, wherein the synthetic clay is selected from the group consisting of layered hydrous magnesium silicate, synthetic mica-montmorillonite, and mixtures thereof.

43. A material according to claim 41, wherein the particles are natural clays selected from the group consisting of hectorite, aliettite, beidellite, nontronite, saponite, sauconite, stevensite, swinefordite, volkonskoite, yakhontovite, montmorillonite, and mixtures thereof.

44. A material according to claim 40, wherein the ligand is selected from the group consisting of quaternary ammonium compounds, organo metallic compounds, ionic polymers, ionic surfactants, and mixtures thereof.

45. A material according to claim 44, wherein the ligand is a quaternary ammonium compound selected from the group consisting of hexadecyltrimethyl ammonium bromide, trimethylphenyl ammonium chloride, and mixtures thereof.

46. A material according to claim 45, wherein the one or more ligands comprise at least two ligands.

47. A material according to claim 46, wherein the at least two ligands are different.

48. A material according to claim 40, wherein the colloid particles have a mean diameter of 1 nm to 1000 $\mu$m.

49. A material according to claim 48, wherein the colloid particles have a mean diameter of 1 nm to 2 $\mu$m.

50. An antimicrobial agent comprising:
   colloid particles having an ion exchange capacity and having attached one or more ligands having antimicrobial properties, wherein the ligands attached to the colloid particles is in a quantity in excess of 100% and up to 200% of the ion exchange capacity of the colloid particles.

51. An antimicrobial agent according to claim 50, wherein the colloid particles are selected from the group consisting of natural clays, synthetic clays, zeolites, hydrotalcite, kaolinite, talc, halloysite, sepiolite, illite, chlorite, and palygorskite.

52. An antimicrobial agent according to claim 51, wherein the colloid particles are synthetic clay selected from the group consisting of layered hydrous magnesium silicate, synthetic mica-montmorillonite, and mixtures thereof.

53. An antimicrobial agent according to claim 51, wherein the colloid particles are natural clays selected from the group consisting of hectorite, aliettite, beidellite, nontronite, saponite, sauconite, stevensite, swinefordite, volkonskoite, yakhontovite, montmorillonite, bentoinite, and mixtures thereof.

54. An antimicrobial agent according to claim 50, wherein the ligand is selected from the group consisting of quaternary ammonium compounds, organo metallic compounds, ionic polymers, ionic surfactants, and mixtures thereof.

55. An antimicrobial agent according to claim 54, wherein the ligand is a quaternary ammonium compound selected from the group consisting of hexadecyltrimethyl ammonium bromide, trimethylphenyl ammonium chloride, and mixtures thereof.

56. The antimicrobial agent according to claim 55, wherein the one or more ligands comprise at least two ligands.

57. The antimicrobial agent according to claim 56, wherein the at least two ligands are different.

58. A complex comprising colloid particles having an ion exchange capacity and having attached one or more ligands, wherein the one or more ligands attached to the colloid particles is in a quantity in excess of 100% and up to 200% of the ion exchange capacity of the colloid particles.

59. A complex according to claim 58, wherein the colloid particles are selected from the group consisting of natural clays, synthetic clays, zeolites, hydrotalcite, kaolinite, talc, halloysite, sepiolite, illite, chlorite, and palygorskite.

60. A complex according to claim 59, wherein the colloid particles are synthetic clay selected from the group consisting of layered hydrous magnesium silicate, synthetic mica-montmorillonite, and mixtures thereof.

61. A complex according to claim 59, wherein the colloid particles are natural clays selected from the group consisting of hectorite, aliettite, beidellite, nontronite, saponite, sauconite, stevensite, swinefordite, volkonskoite, yakhontovite, montmorillonite, bentonite, and mixtures thereof.

62. A complex according to claim 59, wherein the ligand is selected from the group consisting of quaternary ammonium compounds, organo metallic compounds, ionic polymers, ionic surfactants, and mixtures thereof.

63. A complex according to claim 62, wherein the ligand is a quaternary ammonium compound selected from the group consisting of hexadecyltrimethyl ammonium bromide, trimethylphenyl ammonium chloride, and mixtures thereof.

64. A complex according to claim 63, wherein the one or more ligands comprise at least two ligands.

65. A complex according to claim 64, wherein the at least two ligands are different.

66. A method of controlling microbial growth on a surface comprising: applying colloid particles having an ion exchange capacity to the surface in a first step and contacting the colloid particles with one or more ligands having antimicrobial properties in a second step, wherein the colloid particles are selected from the group consisting of natural clays, synthetic clays, zeolites, hydrotalcite, kaolinite, talc, halloysite, sepiolite, illite, chlorite, and palygorskite.

67. A method according to claim 66, wherein the colloid particles are synthetic clay selected from the group consisting of layered hydrous magnesium silicate, synthetic mica-montmorillonite, and mixtures thereof.

68. A method according to claim 66, wherein the colloid particles are natural clays selected from the group consisting of hectorite, aliettite, beidellite, nontronite, saponite, sauconite, stevensite, swinefordite, volkonskoite, yakhontovite, montmorillonite, bentonite, and mixtures thereof.

69. A method according to claim 66, wherein the surface is selected from the group consisting of cellulose, fiberglass, plastics, metals, glass, wood, leather, ceramic, cloth, and painted surfaces.

70. A method according to claim 69, wherein the surface is a filter.

71. A method according to claim 66, wherein the colloid particles have a mean diameter of 1 nm to 1000 $\mu$m.

72. A method according to claim 71, wherein the colloid particles have a mean diameter of 1 nm to 2 $\mu$m.

73. A method of controlling microbial growth on a surface comprising: applying colloid articles having an ion exchange capacity to the surface in a first step and contacting the colloid particles with one or more ligands having antimicrobial properties in a second step, wherein the ligand is selected from the group consisting of quaternary ammonium compounds, antimicrobial metals, organo metallic compounds, perchlorates, charged halogen-containing compounds, charged organic peroxides, ionic polymers, ionic surfactants, and mixtures thereof.

74. A method according to claim 73, wherein the ligand is a quaternary ammonium compound selected from the group consisting of hexadecyltrimethyl ammonium bromide, trimethylphenyl ammonium chloride, and mixtures thereof.

75. A method according to claim 74, wherein the quantity of ligand attached to the colloidal particles is in excess of 100% and up to 200% of the ion exchange capacity of the colloid particles.

76. A method according to claim 75, wherein the one or more ligands comprise at least two ligands.

77. A method according to claim 76, wherein the at least two ligands are different.

78. A method according to claim 73, wherein the antimicrobial metal is a transition metal selected from the group consisting of copper, iron, manganese, zinc, silver, mercury, and mixtures thereof.

79. A method according to claim 73, wherein the surface is selected from the group consisting of cellulose, fiberglass, plastics, metals, glass, wood, leather, ceramic, cloth, and painted surfaces.

80. A method according to claim 76, wherein the surface is a filter.

81. A method according to claim 73, wherein the colloid particles have a mean diameter of 1 nm to 1000 $\mu$m.

82. A method according to claim 81, wherein the colloid particles have a mean diameter of 1 nm to 2 $\mu$m.

* * * * *